United States Patent
Hammon et al.

(10) Patent No.: US 6,806,385 B1
(45) Date of Patent: Oct. 19, 2004

(54) RECTIFICATION OF (METH)ACRYLIC ACID WITH THE ADDITION OF A TENSIDE

(75) Inventors: Ulrich Hammon, Mannheim (DE); Holger Herbst, Frankenthal (DE); Gerhard Nestler, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 151 days.

(21) Appl. No.: 09/622,916

(22) PCT Filed: Mar. 4, 1999

(86) PCT No.: PCT/EP99/01414

§ 371 (c)(1),
(2), (4) Date: Sep. 7, 2000

(87) PCT Pub. No.: WO99/47482

PCT Pub. Date: Sep. 23, 1999

(30) Foreign Application Priority Data

Mar. 13, 1998 (DE) .......................... 198 10 962

(51) Int. Cl.⁷ .......................... C07C 57/42; C07C 27/10
(52) U.S. Cl. .................................... 562/600; 562/512.2
(58) Field of Search .............................. 562/512.2, 600

(56) References Cited

U.S. PATENT DOCUMENTS

| 3,893,895 | A | * | 7/1975 | Denhert et al. |
| 3,932,500 | A | * | 1/1976 | Duembgen et al. |
| 4,496,770 | A | * | 1/1985 | Duembgen et al. |
| 4,600,795 | A | * | 7/1986 | Frank et al. |
| 5,426,221 | A | * | 6/1995 | Willersinn |
| 5,583,084 | A | * | 12/1996 | Martin et al. |
| 5,739,391 | A | * | 4/1998 | Ruppel et al. |
| 5,780,679 | A | * | 7/1998 | Egly et al. |
| 5,821,390 | A | * | 10/1998 | Ruppel et al. |
| 5,855,743 | A | * | 1/1999 | Herbst et al. |

FOREIGN PATENT DOCUMENTS

| CN | 11 053 52 | * | 7/1995 |
| DE | 43 08 087 | * | 9/1954 |
| DE | 2 136 396 | * | 2/1973 |
| DE | 2 235 326 | * | 2/1974 |
| DE | 44 31 949 | * | 3/1995 |
| DE | 44 31 957 | * | 3/1995 |
| DE | 44 05 059 | * | 8/1995 |
| DE | 44 36 243 | * | 4/1996 |
| DE | 197 34 171 | * | 2/1999 |
| EP | 0 092 097 | * | 1/1985 |
| EP | 0 253 409 | * | 1/1988 |
| EP | 0 717 029 | * | 6/1996 |
| EP | 0 722 926 | * | 7/1996 |
| WO | WO 97/36849 | * | 10/1997 |
| WO | WO 98/11048 | * | 5/1998 |

* cited by examiner

Primary Examiner—Johann Richter
Assistant Examiner—Paul A. Zucker
(74) Attorney, Agent, or Firm—Oblon, Spivak, McClelland, Maier & Neustadt, P.C.

(57) ABSTRACT

In a process for rectificative isolation of (meth)acrylic acid from a mixture containing, as main components, (meth)acrylic acid and an organic liquid having a higher boiling point than (meth)acrylic acid, the rectification is carried out with the addition of a surfactant.

15 Claims, No Drawings

RECTIFICATION OF (METH)ACRYLIC ACID WITH THE ADDITION OF A TENSIDE

This application is a 371 of PCT/EP99/01414 filed Mar. 4, 1999.

The present invention relates to a novel process for the rectificative isolation of (meth)acrylic acid from a mixture containing, as main components, (meth)acrylic acid and an organic liquid having a higher boiling point than (meth)acrylic acid.

(Meth)acrylic acid is used as an abbreviated notation that means acrylic acid or methacrylic acid.

(Meth)acrylic acid, either as such or in the form of its esters, is important in particular for the preparation of polymers for a very wide range of applications, for example for use as adhesives.

(Meth)acrylic acid is obtainable, inter alia, by catalytic gas-phase oxidation of alkanes, alkanols, alkenes or alkenals, each of which are of 3 or 4 carbon atoms. (Meth)acrylic acid is easily obtainable, for example, by catalytic gas-phase oxidation of propane, propene, tert-butanol, isobutene, isobutane, isobutyraldehyde or methacrolein. However, other possible starting compounds are those from which the actual $C_3/C_4$ starting compound forms as an intermediate during the gas-phase oxidation. The methyl ether of tert-butanol may be mentioned by way of example.

These starting gases, as a rule diluted with inert gases, such as nitrogen, CO, $CO_2$, saturated hydrocarbons and/or steam, are passed, as a mixture with oxygen at elevated temperatures (usually from 200 to 400° C.) and, if required, superatmospheric pressure, over transition-metal mixed oxide catalysts (containing, for example, Mo, V, W and/or Fe) and are oxidized to (meth)acrylic acid (cf. for example DE-A 4 405 059, EP-A 253 409, EP-A 92 097, DE-A 44 31 957, DE-A 44 31 949, CN-A 11 053 52 and WO 97/36849).

Owing to the numerous simultaneous and subsequent reactions taking place in the course of the catalytic gas-phase oxidation and because of the inert diluent gases present, however, the catalytic gas-phase oxidation does not give pure (meth)acrylic acid but a reaction gas mixture which essentially contains (meth)acrylic acid, the inert diluent gases and byproducts, from which mixture the (meth)acrylic acid must be isolated. In addition to byproducts, for example acetic acid, which are comparatively simple to remove from (meth)acrylic acid and are not very troublesome in subsequent uses of the (meth)acrylic acid, the reaction gas mixture frequently also contains lower aldehydes, such as formaldehyde, acetaldehyde, acrolein, methacrolein, propionaldehyde, n-butyraldehyde, benzaldehyde, furfural and crotonaldehyde, which are closely related to (meth)acrylic acid and therefore difficult to separate from (meth)acrylic acid, and may additionally contain maleic anhydride (the total amount of these byproducts which often present considerable problems in subsequent uses is as a rule $\leq 2$, in general $\geq 0.05$, % by weight, based on the amount of (meth)acrylic acid contained in the reaction gas mixture).

DE-A 44 36 243 relates to a process for isolating (meth)acrylic acid from the reaction gas mixture of the catalytic gas-phase oxidation by countercurrent absorption with a high-boiling inert hydrophobic organic liquid, in which the reaction gas mixture is passed in countercurrent to the descending high-boiling inert hydrophobic organic liquid in an absorption column, a rectification process is superposed on the absorption process taking place in a natural manner in the absorption column, by withdrawing from the absorption column an amount of energy over and above its natural energy output resulting from its contact with ambient temperature, and the (meth)acrylic acid is isolated by rectification from the liquid discharge of the absorption column (absorbate), which discharge contains (meth)acrylic acid and the absorbent as main components and lower aldehydes and possibly maleic anhydride as secondary components. The (meth)acrylic acid obtainable is referred to as crude (meth)acrylic acid. As a rule, it has a purity of >98% by weight.

As high-boiling inert hydrophobic organic liquids (absorbents), DE-A 44 36 243 groups together all those liquids whose boiling point at atmospderic pressure (1 atm) is above the boiling point of (meth)acrylic acid and which comprise at least 70% by weight of molecules which contain no externally acting polar group and, for example, therefore are not capable of forming hydrogen bridges. This concept is applicable here too.

DE-C 2 136 396 and DE-A 43 08 087 also disclose the isolation of acrylic acid from the reaction gas mixture of the catalytic gas-phase oxidation of propylene and/or acrolein by countercurrent absorption with a high-boiling inert hydrophobic organic liquid. The process is carried out essentially by passing the reaction gas mixture in countercurrent to the descending absorption liquid in a conventional absorption column, then, in a desorption column, substantially removing the easily removable readily volatile byproducts from the liquid discharge of the absorption column, which is composed essentially of acrylic acid, the absorbent and byproducts, by stripping with inert gas, and then rectifying the liquid discharge of the desorption column, containing (meth)acrylic acid and the absorbent as main components, for isolation of crude acrylic acid.

DE-A 2 235 326 likewise relates to the problem of the rectificative isolation of (meth)acrylic acid from a mixture thereof with organic solvents having a higher boiling point than (meth)acrylic acid, in particular higher alcohols or esters of these or other alcohols, in particular with (meth)acrylic acid being mentioned in this prior art as possible organic solvents.

However, the disadvantage of the rectificative isolation of crude (meth)acrylic acid or (meth)acrylic acid from mixtures containing (meth)acrylic acid and a high-boiling organic liquid as main components is that the rectification apparatuses (in particular the evaporator surface and column internals) become coated in the course of the rectification. This applies in particular when the mixture to be separated by rectification contains lower aldehydes and possibly maleic anhydride as byproducts. The abovementioned statement is applicable even when polymerization inhibitors, such as phenothiazine, paramethoxyphenol, paranitrosophenol, hydroquinone, hydroquinone monomethyl ether, paraphenylenediamines, N-oxyl compounds and/or air (as mentioned, for example, in DE-A 197 34 171), are concomitantly used for the rectificative separation, in order to suppress the formation of polymeric deposits (formed by free radical polymerization of acrylic acid). The formation of a coating is disadvantageous in that said coating has to be removed from time to time, necessitating a shutdown of the rectification operation.

EP-A 717029 and DE-A 2 235 326 recommend carrying out the rectification with the addition of a primary amine and/or salts thereof for reducing the formation of a coating, but this measure is not completely satisfactory.

For reducing the problem, EP-A 722926 recommends that the starting mixture comprising the (meth)acrylic acid to be isolated by rectification not be fed directly to the rectification column, but first be passed into a heated dwell vessel connected on the vapor side to the rectifier section of the rectification column, in which vessel the starting mixture is kept at the boil, and, instead of the starting mixture as such, the bottom liquid of the dwell vessel be fed to the rectification column; however, this measure too does not completely solve the problem.

It is an object of the present invention to provide a novel process for the rectificative isolation of (meth)acrylic acid from a mixture containing, as main components, (meth)acrylic acid and an organic liquid having a higher boiling point than (meth)acrylic acid, which process, when used alone, permits reduced formation of coatings and hence a longer rectification operation, but which in particular can also be used in combination with the known processes for reducing the formation of coatings.

We have found that this object is achieved by a process for the rectificative isolation of (meth)acrylic acid from a mixture containing, as main components, (meth)acrylic acid and an organic liquid having a higher boiling point than (meth)acrylic acid, wherein the rectification is carried out with the addition of a surfactant.

A surfactant is an amphiphilic substance. This is a substance which has both hydrophilic and hydrophobic groups and is capable of reducing surface tension. Hydrophilic groups are those which are drawn into the aqueous phase whereas hydrophobic groups are expelled from, the aqueous phase.

Surfactants which are capable of reducing the surface tension of water on dissolution therein are particularly suitable according to the invention.

While in highly dilute aqueous solutions water-soluble surfactanrts are present essentially as independent molecules in molecular solution, their amphiphilic structure resulting in accumulation, at the water surface in the form of oriented absorption, which produces a reduction in the surface tension, water-soluble surfactants in concentrated aqueous solutions are dissolved predominantly in micellar form, i.e. the surfactant molecules are arranged in the aqueous solution predominantly in the form of higher aggregates, i.e. micelles, in which they are oriented in such a way that the hydrophilic groups face the aqueous phase and the hydrophobic groups point into the interior of the micelle.

When the surfactant concentration is increased further, essentially only the number of micelles per unit volume increases but not the number of surfactant molecules dissolved in molecular form, per unit volume.

The transition from the aqueous molecular solution to the aqueous micellar solution takes place as a function of the surfactant concentration, usually relatively abruptly, as is evident from correspondingly abrupt change in the concentration dependence of a large number of macroscopic properties, for example the surface tension, and defines the critical micelle formation concentration (usually stated as molar c.m.c.) (point of inflection in the concentration dependence of the properties). At concentrations above the critical micelle formation concentration, the term micellar solutions is used. The term solution is intended to express the fact that a micellar aqueous surfactant solution as well as a molecular aqueous surfactant solution has the same appearance as a clear aqueous solution.

Typical examples of surfactants suitable according to the invention are given, for example, in Ullmanns Encyclopädie der technischen Chemie, Verlag Chemie, 4th edition, Vol. 22, pages 456 to 515.

Surfactants which are particularly suitable according to the invention are those which, on dissolution in water up to the point when the critical micelle formation concentration is reached, are capable of reducing the surface tension $\sigma$ of pure water by at least 15%, based on the corresponding $\sigma$ value of pure water (73 mN/m), at 20° C. and a working pressure of 1 bar.

This means that surfactants suitable according to the invention are those for which the abovementioned reduction of the $\sigma$ value of water up to reaching the c.m.c. is at least 20% or at least 25% or at least 30% or at least 35% or at least 40% or at least 50% or at least 55% or at least 60% or at least 65% or at least 70%.

However, surfactants for which the abovementioned reduction of the $\sigma$ value of water up to reaching the c.m.c. is at least 75% or at least 80% or at least 90% or at least 95% or more are of course also suitable according to the invention.

According to the invention, anionic surfactants, nonionic surfactants, cationic surfactants and/or amphoteric surfactants can in principle be used. Their HLB value can be either >8 or $\leq 8$ (e.g. from 1 to 8) (HLB is the abbreviation for "hydrophilic lipophilic balance"; the HLB value defines the balance of hydrophilic and lipophilic (hydrophobic) groups of the surfactant; a definition of the HLB value is given in "Das Atlas HLB-Systemn", Atlas Chemie GmbH, EC 10 G July 1971, and in "Classification of Surface Active Agents by HLB", W. C. Griffin, Journal of the Society of Cosmetic Chemists, 1 (1949), 311).

When a surfactant combination is used according to the invention, it is merely necessary to ensure that the individual components are compatible with one another. This is not the case, for example, with anionic and cationic surfactants. In principle, the compatibility can be checked in a simple manner in preliminary experiments.

Nonionic and/or cationic surfactants are preferably used according to the invention.

Suitable nonionic surfactants are, for example, all oxyethylates, which in general can be obtained by an addition reaction of ethylene oxide with compounds having mobile protons.

Typical examples of such oxyethylates are the oxyethylates of linear and branched, primary and secondary alcohols of 8 to 30, preferably 12 to 18, carbon atoms, i.e. in particular natural and synthetic fatty alcohols (cf. Ullmanns Encyclopädie der technischen Chemie, Verlag Chemie, 4th edition, Vol. 11, page 427 et seq.), the oxyethylates of alkylphenols having in most cases branched octyl, nonyl or dodecyl radicals, the oxyethylates of fatty acid alkanolamides (for example fatty acid ethanolamides) and fatty amines (cf. Ullmanns Encyclopädie der technischen Chemie, Verlag Chemie, 4th edition, Vol. 11, page 447, et seq.) and the oxyethyiates of esters of the fatty acids with polyhydroxy compounds. Examples of suitable polyhydroxy compounds partially esterified with fatty acids are glycerol, diglycerol, polyglycerol, erythritol, pentaerythritol, xylitol, sorbitol, mannitol and sucrose and other glucosides.

The degree of oxyethylation, i.e. the molar ratio of added ethylene oxide per mole of substrate, may vary within wide limits. As a rule, it is from 3 to 40, frequently from 6 to 30.

It is of course also possible to use substrates oxyalkylated with mixtures of ethylene oxide and propylene oxide or with mixtures of ethylene oxide and butylene oxide, it being possible to vary the choice of ratio of the two epoxides.

Examples of typical members of the abovementioned nonionic surfactants are octylphenol oxyethylates having a degree of oxyethylation of from 4 to 28, oxyethylates of $C_8$- to $C_{20}$-fatty alcohols having a degree of oxyethylation of from 6 to 28 and oxyethylates of $C_8$- to $C_{18}$-fatty amines having a degree of oxyethylation of from 6 to 15.

The incorporation of oxypropyl groups into the molecule of a surfactant increases its hydrophobic character. By subjecting propylene oxide to an addition reaction with a low molecular weight initiator molecule, it is thus possible to prepare hydrophobic parent structures having any desired molar mass. Subsequent oxyethylation of such hydrophobic parent structures obtained gives nonionic surfactants which are suitable according to the invention and which may be formally described as block copolymers of propylene oxide and ethylene oxide. When polyfunctional initiator molecules are used, branches emanate from said molecules. Regarding their use according to the invention, corresponding derivatives of propylene glycol and of ethylenediamine may be singled out in particular by way of example.

By substituting the hydrogen atom of the terminal hydroxyl group of an oxyalkylate by hydrophobic radicals, such as benzyl, butyl or methyl groups, oxyalkylates blocked at the terminal group are obtained, in particular oxyethylates which are blocked at the terminal group and can also be used according to the invention.

Other nonionic surfactants suitable according to the invention are monomers, oligomers and polymers of alkenyl derivatives of 2,5-pyrrolidinedione and of alkenyl derivatives of tetrahydrofuran-2,5-dione. Examples are the products TLA-1605 and TLA-627 from Texaco Additive Company, Belgium (cf. GGC, Rev. 07/07/92,TBTLA-1605.TB and GGC, 16/07/92,TBTLA-627.TB). The relative molecular weight of such surfactants may be, for example, from 200 to 5000.

In contrast to nonionic surfactants which have no ionic groups, the ionic surfactants are amphiphilic compounds in which hydrophobic radicals carry, as hydrophilic groups, anionic or cationic groups which are balanced by opposite ions which have only little effect on the surfactant properties of the substance.

Examples of anionic surfactants suitable according to the invention are the soaps, i.e. the alkali metal and ammonium salts of natural and synthetic fatty acids (cf. Ullmanns Encyclopädie der technischen Chemie, Verlag Chemie, 4th edition, Vol. 21, page 209 et seq.). Advantageous soaps are sodium, potassium and ammonium soaps, particularly when they are $C_8$- to $C_{25}$-soaps.

Other suitable anionic surfactants are the super soaps. These are the alkali metal and ammonium salts (in particular $Na^+$, $K^+$ and $NH_4^+$) of carboxymethylated oxyethylates, suitable oxyethylates being all those mentioned above.

Further anionic surfactants which may be used according to the invention are sarcosides (salts of condensates of fatty acids and amino acids) and sulfonates. Sulfonates are the salts of sulfonic acids in which a hydroxysulfonyl group is bonded directly to a carbon atom of the hydrophobic radical via the sulfur atom. Particularly suitable cationic counterions are the sodium, potassium and ammonium salt and protonated aliphatic amines. Particular examples are p-alkylbenzenesulfonates where the alkyl chain is of 8 to 20 carbon atoms, such as the octyl-, decyl- and dodecylbenzenesulfonates. In particular, alkylbenzenesulfonates where the alkyl radical is of 15 or more carbon atoms dissolve readily in hydrophobic organic solvents, as may also be present in the mixtures to be worked up according to the invention by rectification. Alkylnaphthalenesulfonates, such as dipropyl- and dibutylnaphthalenesulfonates and alkanesulfonates, in particular of 12 to 18 carbon atoms, are likewise suitable according to the invention as antonic surfactants. Finally, further examples of anionc surfactants suitable according to the invention are the alkali metal and ammonium salts (in particular $Na^+$, $K^+$ and $NH_4^+$) of α-sulfofatty acid esters (for example of α-sulfofatty acid mezhyl esters based on coconut, palm kernel or tallow fatty acids), of sulfosuccinic acid mono- and diesters (for example with $C_4$- to $C_8$-alkanols, fatty acid ethanolamides or the oxyethylates thereof (degree of oxyethylation preferably from 3 to 12) as esterification alcohol), of alkoxy-, acyloxy- and acylaminoalkanesulfonic acids, of monoesters of sulfuric acid, of phosphonic acid or of phosphoric acid with primary or secondary $C_8$- to $C_{25}$-alkanols (e.g. hexadecanol or octadecanol) or ethoxylates of these alkanols. The triethanolammonium salts of the abovementioned compounds are also suitable.

Surfactants whose hydrophilic radical is a cation are cationic surfactants. The cationic structure can already be present in the molecule of the surfactant, as in quarternary ammonium or phosphonium salts, but it may also form only after addition to the mixture containing (meth)acrylic acid and to be separated by rectification, as, for example, in oxyethylated fatty amines. Strictly, however, cationic surfactants are to be understood here as meaning only those which do not require protonation with (meth)acrylic acid to become cationic. The cationic surfactants which are most important according to the invention are the quaternary nitrogen compound, in particular the tetraalkylammonium salts, the N,N-dialkylimidazolines and the N-alkylpyridinium salts (e.g. $C_6$- to $C_{20}$-alkyl aroups).

Amphoteric surfactants suitable according to the invention are, for example, ampholytes and betaines. Ampholytes are compounds having at least one mobile proton. Their most well-known members are the aminocarboxylic acids.

According to the invention, it is preferable not to add surfactants which have protonated sulfonic acid groups. It is particularly preferable not to add surfactants which have protonated acid groups whose acidity is greater than that of acrylic acid.

Other surfactants preferred according to the invention are those which have no —$NH_2$ and no —NHR group (where R is an organic radical).

Very generally, those surfactants whose boiling point is >200° C. at 1 bar are preferred. It is also advantageous if the surfactant to be added according to the invention does not decompose at up to 200° C. in the mixture to be treated by rectification. It is also advantageous if the surfactant to be added contains no chemically bound halogen atoms and is ecologically very safe.

The amount of surfactant to be added according to the invention is as a rule from 10 to 5000 ppm by weight, based on the weight of the (meth)acrylic acid-containing mixture to be treated by rectification.

The novel process can be used in particular in the case of mixtures which contain from 5 to 25% by weight of (meth)acrylic acid and from 75 to 95% by weight of organic solvent (based in each case on the weight of the mixture).

Of course, the novel process can be used in combination with the processes described in EP-A 717029 and EP-A 722926 (in each case separately or together).

Preferably used organic solvents are those which essentially do not react with (meth)acrylic acid, i.e. which are inert.

The novel process is of particular importance in the case of methacrylic acid, whose gas-phase catalytic oxidative preparation is carried out using methacrolein as a starting material, particularly when methacrolein is produced by gas-phase catalytic oxidation of tert-butanol, isobutane or isobutene or by reaction of formaldehyde with propionaldehyde according to EP-B 92 097 or EP-B 58 927, in particular when the gas-phase catalytic oxidation of tert-butanol, isobutane or isobutene is carried out with the use of a catalytically active material of the formula I $$Mo_{12}Bi_aFe_bX^1_cX^2_dX^3_eX^4_gO_n \quad (I),$$

where:
- $X^1$ is nickel and/or cobalt,
- $X^2$ is thallium, an alkali metal and/or an alkaline earth metal,
- $X^3$ is phosphorus, arsenic, boron, antimony, tin, cerium, lead, niobium and/or tungsten,
- $X^4$ is silicon, aluminum, titanium and/or zirconium,
- a is from 0.5 bis 5,
- b is from 0.31 bis 3,
- c is from 3 to 10,
- d is from 0.02 to 2,
- e is from 0 to 5,
- g is from 0 to 10 and
- n is an integer which is determined by the valency and frequency of the elements in I other than oxygen, at from 300 to 400° C. and, apart from the special temperature variation, otherwise according to the conditions of DE-A 40 23 239, and the methacrolein obtained is used without intermediate purification for the further oxidation. The novel process also proves useful in particular when, apart from the special temperature variation, the gas-phase catalytic oxidation of the methacrolein is carried out at from 200 to 350° C. according to DE-A 41 32 263 or at from 250 to 400° C. according to DE-A 41 32 684.

The novel process is also particularly suitable in the case of acrylic acid, whose gas-phase oxidative preparation is carried out in one stage starting from acrolein or in two stages starting from propylene, via acrolein. This is true in particular when a multimetal oxide catalyst of the formula II $$Mo_{12}Bi_aFe_bX^1_cX^2_dX^3_eX^4_gO_n \quad (II),$$

where:
- $X^1$ is nickel and/or cobalt,
- $X^2$ is thallium, an alkali metal and/or an alkali earth metal,
- $X^3$ is phosphorus, arsenic, boron, antimony, tin, cerium, lead and/or tungsten,
- $X^4$ is silicon, aluminum, titanium and/or zirconium,
- a is from 0.5 to 5,
- b is from 0.01 to 3,
- c is from 3 to 10,
- d is from 0.02 to 2,
- e is from 0 to 5,
- g is from 0 to 10 and
- n is an integer which is determined by the valency and frequency of the elements other than oxygen, is used for the catalytic gas-phase oxidation of propylene and a multimetal oxide catalyst of the formula III $$Mo_{12}V_aW_bCu_cNi_dX^1_eX^2_fX^3_gX^4_hX^5_iO_n \quad (III)$$

where:
- $X^1$ is one or more alkali metals,
- $X^2$ is one or more alkaline earth metals,
- $X^3$ is chromium, manganese, cerium and/or niobium,
- $X^4$ is antimony and/or bismuth,
- $X^5$ is silicon, aluminum, titanium and/or zirconium,
- a is from 1 to 6,
- b is from 0.2 to 4,
- c is from 0.5 to 6,
- d is from 0.2 to 6,
- e is from 0 to 2,
- f is from 0 to 3,
- g is from 0 to 5,
- h is from 0 r o 40,
- i is from 0 to 40 and
- n is an integer which is determined by the valency and frequency of the elements other than oxygen, is used for the catalytic gas-phase oxidation of acrolein. The reaction gases of the first oxidation stage are usually fed without intermediate purification to the second oxidation stage.

The reaction conditions usually used are described in, for example, DE-A 44 31 957 and DE-A 44 31 949.

The novel process is advantageous in particular when the mixture to be treated by rectification is one which contains (meth)acrylic acid and an inert hydrophobic organic liquid which has a higher boiling point than (meth)acrylic acid, as main components, and lower aldehydes as secondary components (as a rule ≦2% by weight). This applies in particular when the mixture was obtained from the reaction gas mixtures of the abovementioned gas-phase oxidations as the liquid discharge of a countercurrent absorption with subsequent desorption by stripping with an inert gas according to DE-C 2,136,396 or DE-A 43 08 087 or as the liquid discharge of a countercurrent absorption with superposed rectification according to DE-A 44 36 243.

Suitable high-boiling inert hydrophobic organic absorption liquids are in particular all those which are recommended in DE-A 21 36 396 and DE-A 43 08 087. These are essentially liquids whose boiling point at atmospheric pressure is above 160° C. Examples are middle oil fractions from paraffin distillation, diphenyl ether, diphenyl or mixtures of the abovementioned liquids, for example a mixture of from 70 to 75% by weight of diphenyl ether and from 25 to 30% by weight of diphenyl. The use of a mixture containing a mixture of from 70 to 75% by weight of diphenyl ether and from 25 to 30% by weight of diphenyl is advantageous. The use of a mixture containing a mixture of from 70 to 75% by weight of diphenyl ether and from 25 to 30% by weight of diphenyl and, based on this mixture, from 0.1 to 25% by weight of o-dimethyl phthalate is particularly advantageous. Frequently, the high-boiling inert hydrophobic organic liquid is used in the absorption column in amounts such that the liquid discharge contains from 5 to 25, generally from 5 to 15, % by weight of (meth)acrylic acid.

The novel rectificative isolation of (meth)acrylic acid is preferably carried out at reduced pressure, advantageously at a top pressure of ≦100, as a rule from 10 to 100, mbar. In a corresponding manner, the bottom temperatures are from 100 to 22° C. However, said isolation can also be carried out at up to 1 bar.

The novel rectificative isolation of (meth)acrylic acid is advantageously carried out continuously, the (meth)acrylic acid being taken out via the top or a side take-off of the rectification column. The surfactant to be added according to the invention can advantageously be fed to the rectification column above the point of removal of the (meth)acrylic acid. It is noteworthy that the novel procedure results in a reduction in the formation of coatings both in the rectification section and in the stripping section of the rectification column.

Suitable rectification columns are all conventional types, a typical rectification column may be, for example, a bubble tray or packed column. A bubble tray column is preferably used. Advantageously, the position of the continuous feed of the liquid mixture from which the (meth)acrylic acid is to be isolated by rectification is roughly at the end of the first third of the distance between the lowest and highest theoretical separation stage, considered from the lowest theoretical separation stage.

In a continuous procedure, the bottom liquid obtained in the novel rectificative isolation can be removed continuously and, for example, reused directly as absorption liquid in the upstream absorption stage. In order to increase the operating times of the plant, it may be advisable to take off a part-stream of this high-boiling organic liquid and not recycle it until after removal of the absorbent in a working-up stage. Particularly preferably, the total bottom liquid is passed through such a working-up stage before it is recycled to the absorption column. The surfactant to be added according to the invention may of course already be added in the absorption column which effects the isolation of the (meth) acrylic acid from the reaction gas mixture of the catalytic gas-phase oxidation or in any downstream desorption column or in the feed to the rectification column, with the result that direct addition to the rectification column is partly or completely dispensed with. Of course, the novel process is preferably carried out in the presence of customary amounts of conventional polymerization inhibitors, preferably phenothiazine. Usually, they are used in amounts of from 50 to 1000 ppm, based on the weight of (meth)acrylic acid. Furthermore, the novel rectification is preferably operated with airflow.

EXAMPLES

The examples which follow were carried out using a mixture which contained acrylic acid and was obtained as in the example of EP-A 717029.

The mixture contained 14.2% by weight of acrylic acid, 0.02% by weight of acetic acid, 0.01% by weight of furfurols, 0.2% by weight of benzaldehyde, 0.5% by weight of maleic anhydride, 0.1% by weight of water, 0.1% by weight of phenothiazine and, as the remaining amount to 100% by weight, an organic solvent consisting of 57.4% by weight of diphenyl ether, 20.7% by weight of diphenyl and 21.9% by weight of o-dimethyl phthalate.

Example 1

The acrylic acid-containing mixture was passed, at a temperature of 25° C. and at a rate of 3 kg/h, between the fifth and sixth tray (as viewed from the evaporator), into a rectification column which comprised 20 bubble trays and through which air flowed. The rectification column was operated at a bottom temperature of 160° C. and a bottom pressure of 130 mbar and at a top pressure of 80 mbar. Between the fifteenth and sixteenth tray (as viewed from the evaporator), 1300 ml/h of acrylic acid having a purity of 99.7% by weight were removed continuously in liquid form via a side take-off. The mixture arriving at the top of the column and comprising acrylic acid and the components having a lower boiling point than acrylic acid was condensed (600 ml/h), phenothiazine (0.02 g/l) was added as a polymerization inhibitor and, apart from 50 ml/h which were removed, was recycled to the rectification column, above the top bubble tray (upper reflux). Below the side take-off of the acrylic acid, 950 ml/h of the acrylic acid removed were recycled to the column (lower reflux). The continuously removed amount of the bottom liquid was 2580 g/h. After an operating time of 140 hours, the operation of the rectification column had to be stopped owing to the formation of a coating on the column trays in the stripping section and in the rectification section.

Examples 2 to 9

The procedure was as in Example 1, except that in each case from 60 to 120 ppm by weight, based on the amount of reflux, of a surfactant were added to the upper reflux and from 50 to 200 ppm by weight, based on the amount of feed, of the same surfactant were added to the mixture fed to the rectification column. The table below shows the running times achieved as a function of the type and amount of added surfactant used in each case.

| Example | Surfactant | $\sigma_{H2O}$, 0.1 g of surfactant/l, 20° C., 1 bar | Amount in reflux/feed (ppm by weight) | Running time (h) Rectification section/Stripping section |
|---|---|---|---|---|
| 2 | Octylphenol oxyethylate, 25 EO, | 39 mN/m | 60/50 | 830/240 |
| 3 | Octylphenol oxyethylate, 6 EO, | 29 mN/m | 120/110 | 240/240 |
| 4 | Oleylamino oxyethylate, 12 EO, | 35 mN/m | 120/100 | >220/220 |
| 5 | $C_{16}$-/$C_{19}$-fatty alcohol oxyethylate, 25 EO, | 45 mN/m | 60/50 | >350/350 |
| 6 | $C_9$/$C_{11}$-fatty alcohol oxyethylate, 7 EO, 1, 5 BO, | 29 mN/m | 60/50 | 290/290 |
| 7 | PO/EO-block copolymer $[(EO)_x(PO)_{56}(EO)_y, x + y = 8]$ | 36 mN/m | 120/200 | 1160/340 |
| 8 | PO/EO-block copolymer $[(EO)_x(PO)_{56}(EO)_y, x + y = 74]$ | 39 mN/m | 120/200 | >740/>180 |
| 9 | PO/EO-block copolymer $[(EO)_x(PO)_{30}(EO)_y, x + y = 27]$ | 41 mN/m | 120/200 | 620/250 |

EO = ethylene oxide,
PO = propylene oxide,
BO = butylene oxide

We claim:

1. A process for the rectificative isolation of acrylic or methacrylic acid from a mixture containing, as main components, acrylic or methacrylic acid and an organic liquid having a higher boiling point than said acrylic or methacrylic acid, wherein the rectification is carried out with the addition of a surfactant.

2. The process as claimed in claim 1, wherein said surfactant is a nonionic surfactant.

3. The process as claimed in claim 1, wherein said surfactant, on dissolution in water up until reaching the critical micelle formation concentration, is capable of reducing the surface tension of pure water at 20° C. and at a working pressure of 1 bar by at least 15%, based on the corresponding surface tension of pure water.

4. The process as claimed in claim 1, wherein said organic liquid contains diphenyl ether.

5. The process as claimed in claim 1, wherein said organic liquid having a higher boiling point than said acrylic or methacrylic acid is a mixture containing a mixture of from 70 to 75% by weight of diphenyl ether and from 25 to 30% by weight of diphenyl and, based on this mixture, from 0.1 to 25% by weight o-dimethyl phthalate.

6. The process as claimed in claim 1, wherein the mixture containing said acrylic or methacrylic acid contains from 5 to 25% by weight of said acrylic or methacrylic acid.

7. The process as claimed in claim 1, wherein the rectificative isolation is carried out at from 10 to 100 mbar.

8. The process as claimed in claim 1, wherein the rectificative isolation is carried out in the presence of phenothiazine as a polymerization inhibitor.

9. The process as claimed in claim 1, wherein said acrylic or methacrylic acid to be isolated has been produced by catalytic gas-phase oxidation of $C_3$-/$C_4$-starting compounds.

10. A process for the preparation of acrylic or methacrylic acid by catalytic gas-phase oxidation of a $C_3$-/$C_4$-starting compound, in which the reaction gas mixture of the gas-phase oxidation is passed in countercurrent to a descending high-boiling inert hydrophobic organic liquid in an absorption column, the liquid discharge of the absorption column is then stripped with inert gas in a desorption column and said acrylic or methacrylic acid is isolated from the liquid discharge of the desorption column by rectification, wherein the rectificative isolation is carried out with the addition of a surfactant.

11. The process as claimed in claim 3, wherein said surfactant, on dissolution in water up until reaching the critical micelle formulation concentration, is capable of reducing the surface tension of pure water at 20° C. and at a working pressure of 1 bar by at least 75%, based on the corresponding surface tension of pure water.

12. The process as claimed in claim 1, wherein said surfactant is selected from the group consisting of nonionic surfactants and cationic surfactants, and mixtures thereof.

13. The process as claimed in claim 1, wherein said surfactant has a boiling point >200° C. at 1 bar.

14. The process as claimed in claim 1, wherein said surfactant is added in an amount range from 10 to 5000 ppm by weight, based on the weight of said acrylic or methacrylic acid containing mixture.

15. The process as claimed in claim 1, wherein said surfactant is selected from the group consisting of anionic surfactants, nonionic surfactants, cationic surfactants and amphoteric surfactants, and mixtures thereof.

* * * * *

UNITED STATES PATENT AND TRADEMARK OFFICE
CERTIFICATE OF CORRECTION

PATENT NO. : 6,806,385 B1
DATED : October 19, 2004
INVENTOR(S) : Hammon et al.

It is certified that error appears in the above-identified patent and that said Letters Patent is hereby corrected as shown below:

Title page,
Item [*] Notice, delete "151" and insert -- 703 --.

Signed and Sealed this

Tenth Day of January, 2006

JON W. DUDAS
*Director of the United States Patent and Trademark Office*